United States Patent [19]

Kamen

[11] 4,410,164

[45] Oct. 18, 1983

[54] MODULAR FLOW CONTROL SYSTEM

[75] Inventor: Dean L. Kamen, Bedford, N.H.

[73] Assignee: Baxter Travenol Laboratories, Inc., Deerfield, Ill.

[21] Appl. No.: 336,068

[22] Filed: Dec. 31, 1981

[51] Int. Cl.³ .................... F61L 55/14; A61M 5/00
[52] U.S. Cl. .................................. 251/9; 604/34; 604/250
[58] Field of Search .......... 128/214 R, 214 C, 214 F; 251/8, 9; 604/34, 250, 251

[56] References Cited

U.S. PATENT DOCUMENTS

| | | | |
|---|---|---|---|
| 2,931,387 | 4/1960 | Fleming | 251/9 X |
| 4,136,692 | 1/1979 | Goldowsky | 128/214 C |
| 4,300,552 | 11/1981 | Cannon | 128/214 F |
| 4,328,946 | 5/1982 | Morin | 251/9 |

*Primary Examiner*—Stephen C. Pellegrino
*Attorney, Agent, or Firm*—Bromberg, Sunstein & McGregor

[57] ABSTRACT

In a system for controlling flow of fluid from a reservoir to be delivered intravenously to a patient, a valve adjustably constricts a fluid path and maintains a given adjustment until the adjustment is changed. In a preferred embodiment, a valve assembly is insertable into a servo assembly that controls flow through the valve. The valve can be removed from the servo assembly and, when so removed, will retain its last adjustment. A preferred embodiment of the valve utilizes a screw to compress a tube of resilient material.

14 Claims, 4 Drawing Figures

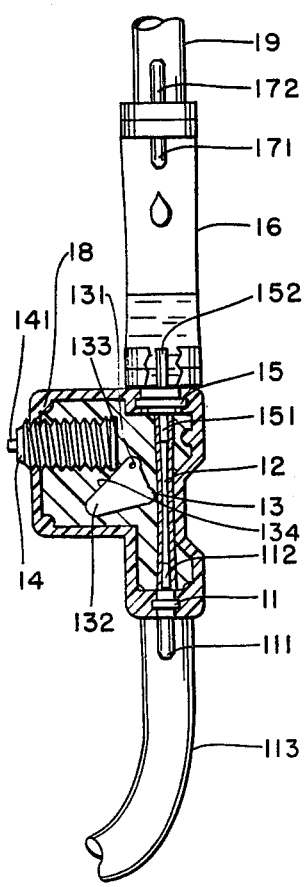
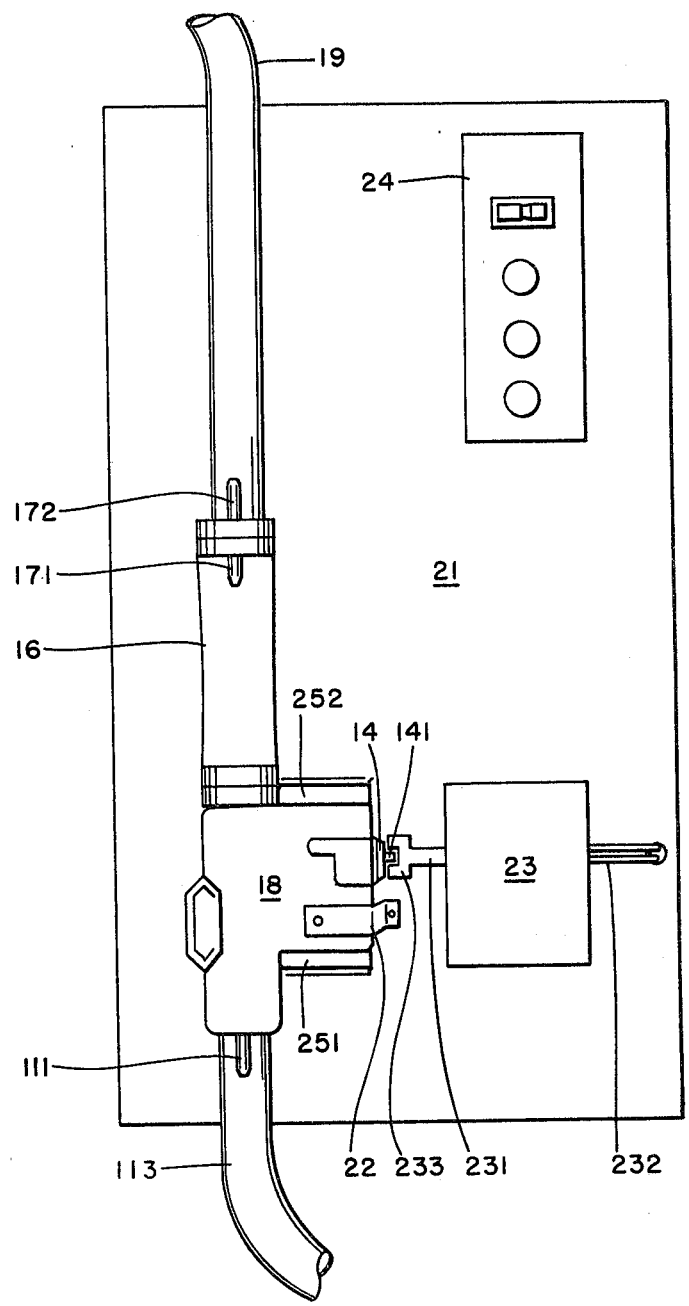
Fig. 1
Fig. 2

MODULAR FLOW CONTROL SYSTEM

DESCRIPTION

TECHNICAL FIELD

The present invention relates generally to fluid flow control systems, and particularly to systems for controlling flow of fluid from a reservoir to be delivered intravenously to a patient.

BACKGROUND ART

Manual intravenous systems typically control flow by means of roller clamp devices. Such devices have the virtue of simplicity, but are sometimes difficult to adjust and are not amenable to insertion in a servo assembly for automatic control of flow rate. Moreover, such manual devices may not permit control of flow rate with sufficient precision. On the other hand, automatic flow control devices commonly require insertion directly in the flow path of the fluid, and in instances when indirect mechanical control of flow is achieved without insertion into the flow path, there are problems in achieving a fail-safe mode of operation and in permitting disengagement of the control device in such a way that flow continues at a rate last adjusted by the device.

DISCLOSURE OF INVENTION

The present invention provides a valve for adjustably constricting a fluid path and for maintaining a given adjustment until the adjustment is changed. In a preferred embodiment, a valve assembly is insertable into a servo assembly that controls flow through the valve. The valve can be removed from the servo assembly and, when so removed, will retain its last adjustment. A preferred embodiment of the valve utilizes a screw to compress a tube of resilient material.

BRIEF DESCRIPTION OF THE DRAWINGS

The invention will be more readily understood by consideration of the following detailed description taken with the accompanying drawings, in which:

FIG. 1 shows a partial cut away view of a preferred embodiment of the invention utilizing a drip chamber valve assembly;

FIG. 2 shows a servo assembly with the drip chamber valve assembly of FIG. 1 positioned therein;

DESCRIPTION OF SPECIFIC EMBODIMENTS

Figure 3:
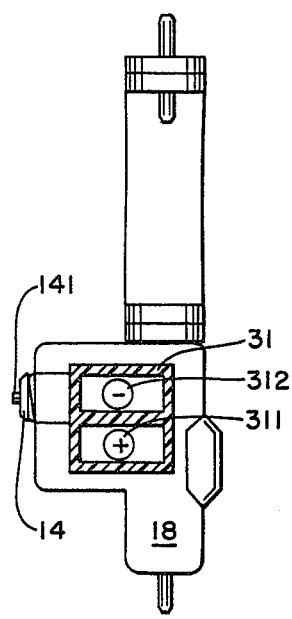
FIG. 3 shows a view of the assembly of FIG. 1 but without the cut away.

Referring to FIG. 1, the drip chamber valve assembly includes a drip chamber 16 mounted on a case 18. The case 18 includes a valve as discussed below. Fluid enters the drip chamber valve assembly through an inlet tube 19 and leaves through an exit tube 113. The drip chamber 16 is formed by a generally cylindrical resilient and transparent member sealed at the top and at the bottom. Through the seal at the top, however, is a fluid passageway formed by an inlet port 172 (connected to the inlet tube 19) and a drip nozzle 171 (connected to the inlet port 172). Fluid leaves the drip chamber 16 through a passageway formed by the drip chamber exit port 152. The exit port 152 is in communication with middle disk assembly 15, which is mounted in the case 18. Part of the disk assembly includes constriction input 151, so that fluid flow is directly from the drip exit port 152 through the constriction input 151. The constriction input is attached concentrically within the constriction tube 12. The constriction tube 12 is a length of resilient tube, in this case of silicon rubber of the type marketed by General Electric under the Selastic brand name. The constriction tube 12 in turn is attached at its lower end to an output 112 that is in communication with exit port 111. The constriction tube output 112 and exit port 111 are part of a lower disk assembly 11 that is held in place by the case 18.

In operation of the drip chamber valve assembly, the cam 132 has a lobe 113 that is in contact with the constriction tube 12 to compress it against the case. The cam has a pivot 133 about which it is rotationally displaced in response to the displacement of the tip 133 of a screw 14 against it. The screw tip 133 comes in contact with a surface 134 of the cam on the opposite side of the pivot 133 from the lobe 13. The screw 14 is threaded into the case 18 and can be adjusted by turning the head 141. Careful adjustment of the geometry of the cam 132 can permit pecise adjustment of the amount of constriction in the constriction tube 12 and thereby the flow rate. Of course the thread pitch of the screw 14 is also a factor, but I have found that even with a relatively course threading of the screw 14, a satisfactory adjustment can be readily achieved. It can be seen that once an adjustment of flow rate has been achieved by appropriate turning of the screw 14 by its head 141, the adjustment will not change if the drip chamber valve assembly is left unattended, since the cam 132 will not cause rotation of the screw 14 in a proper design.

It is important in most applications for the tube to tend to return to its original shape when pressure from cam lobe 13 against it is reduced, so that the flow rate will increase as the tip 133 of the screw is withdrawn from contact with the cam 132. It should be noted that the shape of cam edge 134 will affect the response characteristics of the valve assembly. For example, if it is desired to compensate for nonlinearities in response of the constriction tube to pressure, it may be desirable to alter the shape of the cam edge 134 from the relatively straight line shown. Thus, as the screw 114 is advanced into the case, any desired rate of change of contriction in the constriction tube 12 can be accomplished by suitable configuration of the shape of cam edge 134.

In FIG. 2 is shown a servo assembly 21 with the drip chamber valve assembly of FIG. 1 in place. The case 18 is held in place by the guides 251 and 252, which prevent vertical motion of the case 18. Horizontal motion toward and away from the servo assembly 21 is restricted by bracket 22. Rotational displacement of the screw 14 is effected by a motor 23 coupled via a shaft 231 and coupler 233 to the screw head 141. Although this embodiment shows a tongue (screw head 141) and groove (the slot in coupler 233) coupling, any suitable coupling arrangement can be used. In many instances it may be desirable to cause the tip of the shaft 231 to be fluted and to provide a suitable receptacle for the fluted shaft in the head of the screw 14. The motor 23 is powered by the leads 232 and, since the device retains its last adjustment, the motor 23 may be, for example, a stepping motor having a capability of orienting the shaft 231 (and thereby the screw 14) at any desired rotational displacement. The motor 23, of course, need be actuated only when flow rate needs to be changed. This feature provides dramatically reduced power drain in comparison to many prior art devices. The flow rate itself can be monitored either by conventional means of monitoring drip rate through the drip chamber 16 or monitoring the flow at any other suitable point in the flow path. Flow may also be monitored in accordance with the invention described in my co-pending patent application Serial No. 254,304, filed Apr. 15, 1981. The servo assembly also includes a control panel 24. Other features of the drip chamber valve assembly are a identified in FIG. 1. (Throughout the description and figures herein, a given number identifies uniformly the same item in each of the figures.)

The drip chamber valve assembly is designed to be simple enough that it may be disposed as part of a cassette system after a single use. The servo assembly may be powered by its own internal battery or by conventional alternating current power sources. As yet another alternative, however, owing to its low power consumption, the servo assembly may be powered by a small battery contained in the drip chamber valve assembly. In embodiments when the drip chamber valve assembly is discarded after a single use, the placement of a battery in the drip chamber valve assembly will assure that fresh battery power is available to the servo assembly for each new use. A preferred embodiment of this design is shown in FIG. 3, which presents a view of the drip chamber valve assembly without the cut away. The assembly includes a battery 31 having terminals 311 and 312. This battery may be the flat type of battery resently introduced in connection with film for loading into SX-70 brand instant cameras manufactured by the Poloroid. Alternatively, the drip chamber valve assembly may employ one or more button type batteries connected to suitable output terminals.

Figure 4:
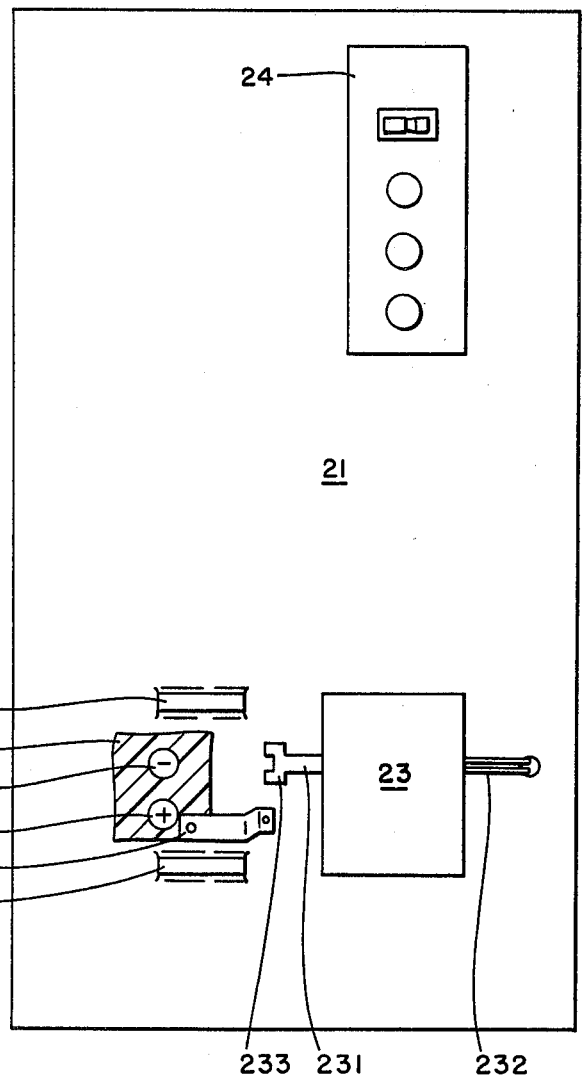
FIG. 4 presents a view of the servo assembly without the drip chamber valve assembly in place.

When the drip chamber valve assembly of FIG. 3 is inserted into the servo assembly of FIG. 4, the battery terminals 311 and 312 mate with corresponding terminals 411 and 412 on terminal strip 41 of the servo assembly 21.

It should be noted that in the event of a power failure to the servo assembly 21, or in the event of its total failure, the drip chamber valve assembly retains its last setting. There is no catastrophic failure. Moreover, in the event of such a failure, the drip chamber valve assembly can be removed expediently from the servo assembly and controlled either manually or by other suitable means.

Accordingly, while the invention has been described with particular reference to specific embodiment thereof, it will be understood that it may be embodied in a variety of forms diversed by those shown and described without departing from the spirit and scope of the invention as defined by the following claims.

What is claimed is:

1. A flow control system comprising:
   a case;
   a tube of resilient material, of which at least a portion is located within the case;
   a threaded member, having a thread axis and mounted in the case, to cause adjustable compression of the tube as the threaded member is advanced, by bearing against a movable member in contact with the tube; and
   a movable member having a first face in contact with the tube and a second face contacted by the threaded member, said second face being aligned at a substantially oblique angle, and the first face being substantially non-parallel, with respect to the thread axis, so that axial motion of the threaded member causes a functionally proportional degree of motion of the first face for compressing the tube.

2. A system according to claim 1, wherein the movable member is a cam pivotally mounted in the case, the angular position of which cam with respect thereto is affected by the threaded member, and wherein the first face is a lobe surface (hereinafter, the "clamp surface") in contact with the tube.

3. A system according to claim 2 wherein the second face is a surface generally opposite to the clamp surface.

4. A system according to claim 3, further comprising:
   a drip chamber in communication with the tube.

5. A system according to claim 4, further comprising:
   servo means for releasably receiving and holding the case and releasably driving the threaded member, and, while the case is being held, for controlling flow by adjusting angular displacement of the threaded member.

6. A system according to claim 5, further comprising:
   a battery, physically attached to the case, for powering the servo means when the case is being held thereby.

7. A system according to claim 1, further comprising:
   a drip chamber in communication with the tube.

8. A system according to claim 2, further comprising:
   a drip chamber in communication with the tube.

9. A system according to claim 8, further comprising:
   servo means for releasably receiving and holding the case and releasably driving the threaded member, and, while the case is being held, for controlling flow by adjusting angular displacement of the threaded member.

10. A system according to claim 9, further comprising:
    a battery, physically attached to the case, for powering the servo means when the case is being held thereby.

11. A system according to claim 2, further comprising:
    servo means for releasably receiving and holding the case and releasably driving the threaded member, and, while the case is being held, for controlling the flow by adjusting angular displacement of the threaded member.

12. A system according to claim 10, further comprising:
    a battery, physically attached to the case, for powering the servo means when the case is being held thereby.

13. A system according to claim 1, further comprising:
    servo means for releasably receiving and holding the case and releasably driving the threaded member, and, while the case is being held, for controlling flow by adjusting angular displacement of the threaded member.

14. A system according to claim 13, further comprising:
    a battery, physically attached to the case, for powering the servo means when the case is being held thereby.

* * * * *